US008574242B2

(12) United States Patent
Pfeiffer et al.

(10) Patent No.: US 8,574,242 B2
(45) **Date of Patent: *Nov. 5, 2013**

(54) EPILATOR WITH AN ATTACHMENT AND SUCH ATTACHMENT

(75) Inventors: Bernd Pfeiffer, Schwalbach (DE); Frieder Grieshaber, Neu-Anspach (DE); Bernhard Kraus, Braunfels (DE)

(73) Assignee: Braun GmbH, Kronberg (DE)

( * ) Notice: Subject to any disclaimer, the term of this patent is extended or adjusted under 35 U.S.C. 154(b) by 70 days.

This patent is subject to a terminal disclaimer.

(21) Appl. No.: 13/184,792

(22) Filed: Jul. 18, 2011

(65) Prior Publication Data

US 2011/0276061 A1 Nov. 10, 2011

(30) Foreign Application Priority Data

Feb. 18, 2009 (EP) .................................... 09002259

(51) Int. Cl.
*A61B 17/50* (2006.01)

(52) U.S. Cl.
USPC .......................................................... 606/133

(58) Field of Classification Search
USPC ............................ 606/131, 133; 30/34.05, 50
See application file for complete search history.

(56) References Cited

U.S. PATENT DOCUMENTS

| | | | | |
|---|---|---|---|---|
| 4,922,608 A * | 5/1990 | Pahl | 30/43.91 |
| 5,108,410 A | 4/1992 | Iwasaki et al. | |
| 5,171,315 A * | 12/1992 | Cabrero | 606/131 |
| 5,507,753 A * | 4/1996 | Iwasaki et al. | 606/133 |
| 5,810,843 A * | 9/1998 | Iwasaki et al. | 606/133 |
| 5,916,222 A * | 6/1999 | Iwasaki et al. | 606/133 |
| 5,980,452 A * | 11/1999 | Garenfeld et al. | 600/133 |
| 6,004,331 A * | 12/1999 | Takeuchi et al. | 606/133 |
| 6,740,097 B1 * | 5/2004 | Sanchez-Martinez | 606/133 |
| 7,147,645 B2 * | 12/2006 | Sanchez-Martinez et al. | 606/133 |
| 8,109,001 B2 * | 2/2012 | Royle et al. | 30/34.1 |

(Continued)

FOREIGN PATENT DOCUMENTS

DE 102005061490 A1 7/2007

OTHER PUBLICATIONS http://www.thefreedictionary.com/shave, dictionary definition of the term “shave”.*
http://www.thefreedictionary.com/pluck, dictionary definition of the term “pluck”.*
International Search Report dated May 18, 2010, 3 pages.

*Primary Examiner* — Ryan Severson
*Assistant Examiner* — David Eastwood
(74) *Attorney, Agent, or Firm* — David K Mattheis; Brent M Peebles

(57) ABSTRACT

The present invention is concerned with an epilator that comprises a housing, an epilation cylinder mounted at a head region of the housing for plucking hairs from the skin during operation, and an attachment detachably connected with the housing, which attachment comprises at least a shaving blade defining a use direction along which the shaving blade is to be drawn over the skin to shave off hairs. In the attached state the shaving blade is disposed behind the epilation cylinder with respect to the use direction so that during operation the epilation cylinder plucks hairs from the skin and the shaving blade contacts the skin to shave off hairs from the skin in successive order during a single stroke of the epilator over a skin area, wherein the attachment is connected with the housing in the head region such that the epilation cylinder is partially covered by the attachment and a non-covered part of the epilation cylinder extends into an aperture of the attachment.

5 Claims, 2 Drawing Sheets

(56) References Cited

U.S. PATENT DOCUMENTS

| | | | | |
|---|---|---|---|---|
| 2002/0088122 | A1* | 7/2002 | Zuidervaart | 30/50 |
| 2006/0004383 | A1* | 1/2006 | Floessholzer et al. | 606/133 |
| 2007/0066979 | A1* | 3/2007 | Beytollahi | 606/133 |
| 2008/0086887 | A1 | 4/2008 | Park et al. | |
| 2008/0216320 | A1* | 9/2008 | Royle et al. | 30/34.1 |
| 2008/0301947 | A1 | 12/2008 | Dorber et al. | |
| 2010/0234858 | A1 | 9/2010 | Sanchez-Martinez et al. | |
| 2010/0274261 | A1* | 10/2010 | Grieshaber et al. | 606/133 |
| 2012/0041452 | A1* | 2/2012 | Grieshaber et al. | 606/133 |

* cited by examiner

EPILATOR WITH AN ATTACHMENT AND SUCH ATTACHMENT

CROSS REFERENCE TO RELATED APPLICATION

This application is a continuation of prior co-pending International Application No. IB2010/050565, filed Feb. 8, 2010 designated the United Sates.

FIELD OF THE INVENTION

The present invention is concerned with an epilator that has an attachment and it is further concerned with such an attachment.

BACKGROUND OF THE INVENTION

From international patent application WO 2007/033746 A1 an attachment for a shaver or an epilator is known, which attachment comprises a polishing body (an abrasive element) for polishing the skin that is shaved or epilated to abrade e.g. dead skin particles and to improve the skin smoothness.

It is now desirable to provide an epilator with an attachment and an attachment for an epilator that provide further functionality and comfort for the user.

SUMMARY OF THE INVENTION

Such an epilator with an attachment is described by the present invention.

The epilator according to a first embodiment has a housing, an epilation cylinder mounted at a head region of the housing and an attachment. The attachment is detachably mounted to a head region of the epilator such that the epilation cylinder is partially covered. Hence, the attachment is an aesthetic measure as it completes the outer appearance of the epilator and it further is a security measure as it partially covers the epilation cylinder that is rotating at a considerable speed during operation. Further, the attachment has an aperture into which the non-covered part of the epilation cylinder extends for contacting the skin during operation and for clamping and plucking out hairs. The attachment also comprises a shaving blade (or several shaving blades) that is disposed behind the epilation cylinder with respect to the use direction of the epilator (which means that the use direction of the epilation cylinder and the use direction of the shaving blade coincide; in other words: the epilation cylinder is then arranged in front of the shaving blade with respect to the use direction of the shaving blade). The shaving blade (or shaving blades) contacts the skin during operation such that hairs that are not plucked from the skin due to the naturally non-perfect plucking efficiency of the epilation cylinder are shaved off in the same single stroke (where the "plucking efficiency" is defined as the ratio of hairs plucked per skin area in a single stroke over the hairs present on the skin area before the epilation procedure). By this specific combination the proposed epilator overcomes the widely known prejudice that epilation and shaving are two separate hair removal technologies and that a user. will either shave or epilate, but not both together. Now, it was discovered that the combination of an epilation cylinder arranged before a shaving blade (with respect to the use direction) allows for almost complete hair removal in a single stroke, hence allows for a hair removal efficiency of almost 100% in a single stroke (total hair removal efficiency depends on the speed with which the epilator is drawn over the skin and the number of shaving blades). This saves valuable hair removal time and also the plucking pain during the procedure is reduced as the user does not need to epilate the area several times until the hairs are plucked completely. Additionally. the shaved skin feels smooth and clean, which is an essential improvement over the dry and itchy feeling of skin that is purely epilated. Hence, this kind of an epilation and shaving combination is not only theoretically beneficial but also surprisingly well received by users.

In another embodiment, the attachment comprises a first (or outer) frame structure and a second (or inner) frame structure and the aperture and the shaving blade (or blades) are part of the second frame structure. Further, the second frame structure is mounted to the first frame structure so as to enable swiveling of the second frame structure with respect to the first frame structure. This allows e.g. to couple the swiveling second frame structure with the epilation cylinder and to shift the clamping point in accordance with the swivel angle so that the clamping point is fixed with the second frame structure. In such a realization, the user can use the epilator in different angulations of the housing with respect to the skin while the clamping point is fixed with respect to the skin-contacting second frame structure.

In a refinement of the previous embodiment, the second frame structure is also detachably mounted to the first frame structure. This allows specifically realizing the second frame structure as a disposable unit.

In another embodiment, the attachment comprises a first frame structure, a shaving blade cartridge into which at least a shaving blade is integrated, and a coupling structure for releasably coupling the shaving blade cartridge to the first frame structure. This allows realizing the shaving blade cartridge as a disposable unit. In a refinement of this embodiment, the shaving blade cartridge is pivotably mounted with respect to the first frame structure. This means that by applying the epilator against the skin, the shaving blade cartridge follows the skin topology better than in case of a rigid mounting. As the contact area comprising epilation cylinder and shaving blade is relatively large, this leads to improved skin contact of the epilation cylinder and the shaving blade and hence to improved hair removal efficiency.

The invention also is concerned with an attachment that can be detachably connected to a housing of an epilator so that an epilator is formed. The attachment has an aperture and a shaving blade that is arranged behind the aperture with respect to the use direction of the shaving blade. The aperture is arranged such that an epilation cylinder mounted to the head region of the housing extends into the aperture for plucking hairs in the connected state of the attachment and the attachment is then also partially covering the epilation cylinder.

BRIEF DESCRIPTION OF THE DRAWINGS

The proposed epilator comprising an attachment and the attachment will be further elucidated by description of exemplary embodiments and by references to Figures. In the figures

DETAILED DESCRIPTION OF THE INVENTION

Figure 1:
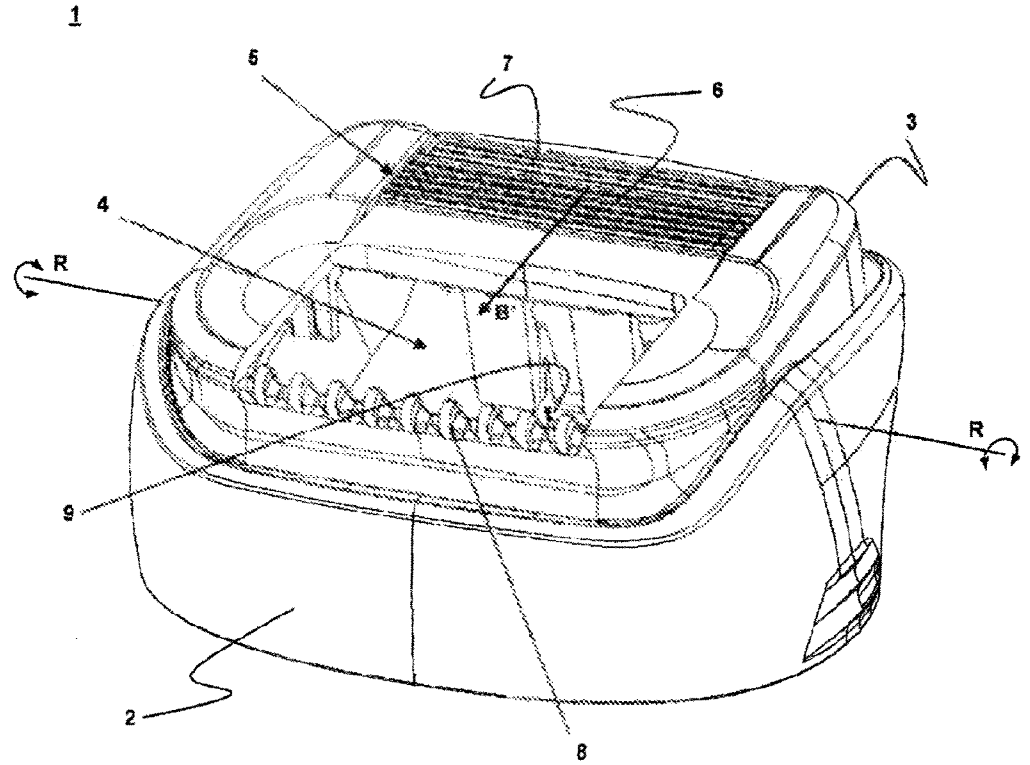
FIG. 1 depicts an exemplary attachment as proposed and FIG. 2 is a depiction of an epilator that comprises the attachment as shown in FIG. 1.

FIG. 1 is a depiction of an exemplary embodiment of an attachment 1 as proposed. The shown attachment comprises a first (or outer) frame structure 2. The first frame structure 2 has at least a first connector element 9 (here: a recess) for detachably connecting the attachment 1 to a head region of an epilator at which appropriate second connector structures are provided; e.g. the housing of the epilator could be equipped with one or several hooks that snap-fit into recesses provided in the first frame structure 2 (or vice versa) to detachably connect the housing and the attachment 1. The shown attachment 1 further has a second (or inner) frame structure 3, which is mounted to the first frame structure 2 such that the second frame structure 3 can swivel around a swivel axis R with respect to the first frame structure 2. The second frame structure 3 has an aperture 4 in its top area, which top area is intended for contacting the skin of a person in a use operation of the epilator with the attachment 1 connected. The aperture 4 is dimensioned such that in the mounted state an epilation cylinder of the epilator extends into the aperture 4 and is then arranged to contact the skin during operation for plucking out hairs from the skin. This will be explained further with reference to FIG. 2. The top area of the second frame structure 3 may be equipped with a soft material for a gentle skin contact. The second frame structure 3 may hence consist of the soft material or could be laminated with the soft material. The soft material could be synthetic or natural rubber.

In the shown embodiment, a blade block 5 comprising a plurality of shaving blades 6 (here: five blades) is fixedly integrated into the second frame structure 3. Alternatively, every other number of shaving blades could be comprised in the blade block 5, e.g. two blade, three blades, four blades, six blades etc. Instead of a blade block 5, a single shaving blade 6 could be integrated into the second frame structure 3. The orientation of the blades 6 (or single blade) with respect to the top area of the second frame structure 3 is such that the sharp blade edges contact the skin during operation in the same manner as it would if the blade block 5 were integrated into a safety razor (e.g. a Gillette Venus Breeze safety razor). The shaving blade (or shaving blades) then define a use direction B' of the shaving blade 6 (or shaving blades) along which the attachment I is to be drawn over the skin to shave off hairs; the shaving blade (or shaving blades) are arranged behind the aperture 4 with respect to the use direction B' of the shaving blade. In addition to the blade block 5 (or the single shaving blade 6), soft skin-tightening lamellae 7 and/or one or several lubrication strips and/or one or several applicator units releasing a refreshing material and/or lathering surfactant during the use operation could be integrated into the second frame structure 3.

In an alternative embodiment. the attachment 1 has only a single first frame structure into which the blade block 5 or the single blade 6 is integrated and into which also the other features (lamellae, strips, applicator unit) as listed before could be integrated. In even another embodiment. the blade block 5 or the single blade 6 is integrated into a blade cartridge that can be detachably connected to the second frame structure 3 (or the single first frame structure) via a coupling system as is generally known in the art of safety razors; alternatively, the blade block 5 or the single blade 6 could be integrated into a sub-frame structure of either the single first frame structure or of the shown second frame structure 3, which sub-frame structure is arranged to e.g. detachably snap-fit to the single first frame structure or the second frame structure 3. In an embodiment with a detachable blade cartridge or a detachable sub-frame structure, the blade cartridge or the sub-frame structure is realized as a disposable unit. In an embodiment with an integrated blade block 5 or single blade 6, either the second frame structure 3 or the whole attachment 1 is realized as a disposable unit that can be replaced by a new attachment, e.g. when the blade or blades 6 are not sharp anymore or if another user is going to use the epilator with a personalized attachment.

The longitudinal extension length of the blade 6 or blades and the axial length of the epilation cylinder extending into the aperture are chosen to be equal and further they are positioned such that they cover the same skin region when the device is drawn over the skin during operation to avoid that e.g. the shaving blade shaves areas were the epilation cylinder has not plucked hairs previously, which would result in certain skin stripes on which hairs would grow faster than at other skin areas.

The second frame structure 3 further comprises a frontal comb structure 8; alternatively to such a comb structure 8, a skin stimulation structure (e.g. comprising spiked rolls, as is known in the art) could be arranged in front of the aperture with respect to the use direction.

Figure 2:
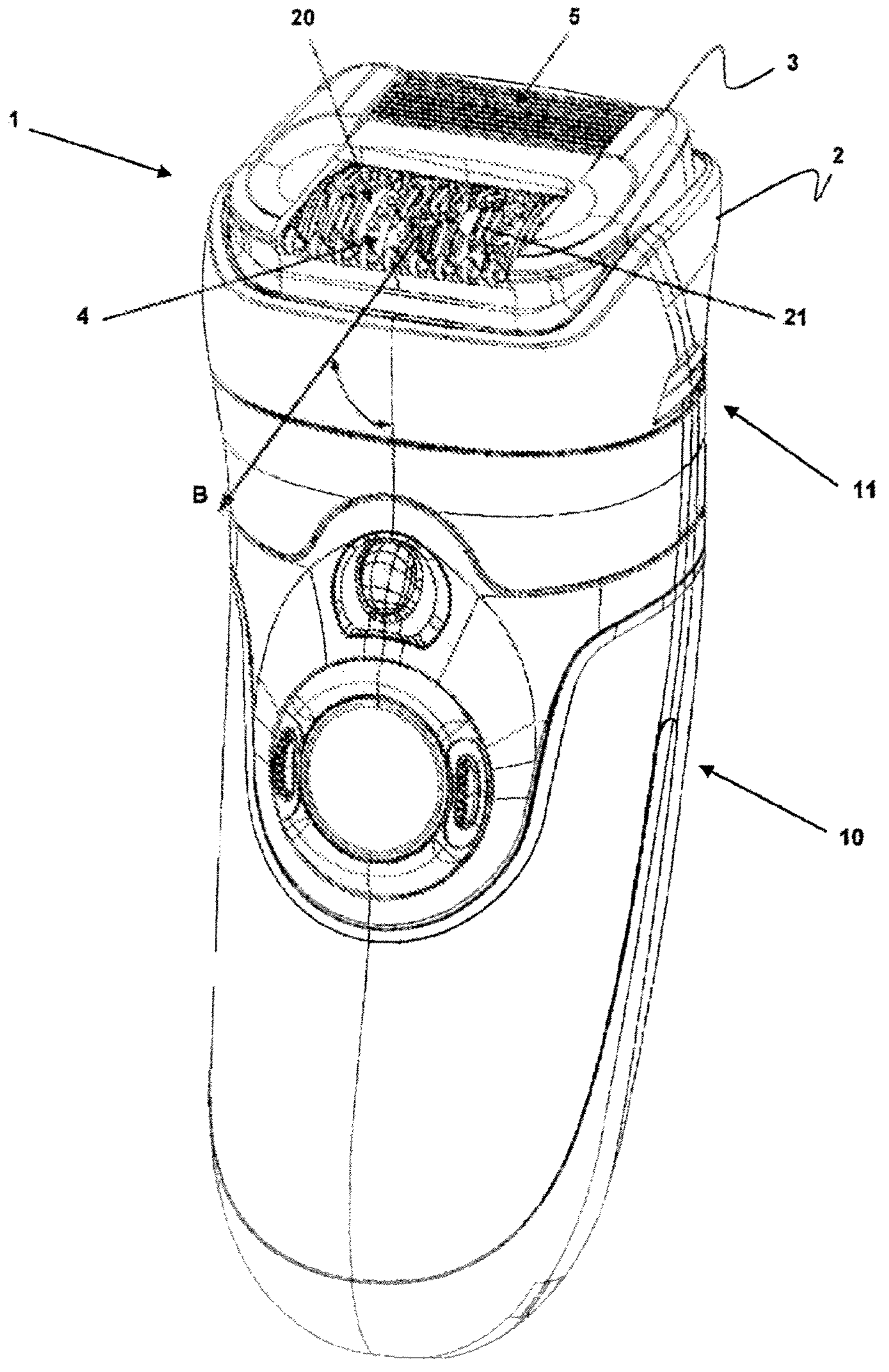

In FIG. 2 an epilator 100 is shown, which epilator comprises a housing 10, an epilation cylinder 20 mounted to the head region 11 of the epilator 100 and an attachment 1 as shown in FIG. 1 detachably mounted to the head region of the epilator 100 such that the epilation cylinder 20 is partially covered by the attachment 1 and the non-covered part extends into the aperture 4 of the attachment 1. The epilation cylinder 20 may be designed as is described in international patent application WO 2006/037392 A1, which document is herewith incorporated by reference. The epilation cylinder 20 comprises pairs of clamping elements 21. The epilation cylinder 20 is set into rotation during operation of the epilator 100. The pairs of clamping elements 21 are closed in a clamping region that lies in the aperture and the pairs of clamping elements 21 are kept in the closed position for a certain rotational angle to keep hairs clamped and thus ultimately pluck them out from the skin while the epilation cylinder 20 continues to rotate. As this motion sequence of the pairs of clamping elements 21 is not symmetrical with respect to the skin contact region, the epilator 100 has a distinct inherently given (preferred) use direction B along which the epilator 100 is to be drawn over the skin to enable efficient plucking of hairs. Here, the use direction B is fixed to the second frame structure 3, which can be wivelled around the swivel axis R (as indicated in FIG. 1) to allow the user to find an optimal angularity of the epilator housing 10 with respect to the skin or to change the angularity (within certain limits) in dependence on the skin area to be epilated. In the connected (or mounted) state of the attachment 1, the blade 6 or the blade block 5 is positioned behind the epilation cylinder 5 with respect to the (preferred) use direction B (or in other words, as the shaving blade 6 has only a single use direction B' and is useless when drawn along the opposite direction, the epilator 100 has only a single use direction B that allows hair removal by the epilation cylinder 20 and the shaving blade 6 in successive order in a single stroke and the shaving blade 6 is arranged behind the epilation cylinder 20 with respect to this use direction B). The use direction B' of the shaving blade 6 coincides with the preferred use direction B of the epilation cylinder 20, hence drawing the epilator 100 along the use direction B over the skin allows for successive plucking of hairs by the epilation cylinder as a first hair removal procedure and shaving off hairs by the shaving blade as a second hair removal procedure in a single stroke of the epilator 100 over a given skin area. Hence, if the epilator 100 is drawn over the skin along the use direction B, hairs feed in between the pairs of clamping elements 21, which hairs are clamped by the closing pairs of clamping elements 21 and are then plucked out from the skin when the closed pairs of clamping elements 21 further rotate with the rotating epilation cylinder 20. The plucking efficiency (which is the ratio of hairs that are plucked in a single stroke from a certain skin area over the hairs that were present on that skin area before the plucking procedure) is dependent on several parameters such as the density of the pairs of clamping elements 21 on the epilation cylinder 20, the speed with which the epilator is drawn over the skin, the rotational speed of the epilation cylinder 20 etc. The plucking efficiency hardly becomes 100% and usually is lower, which means that hairs remain in the skin after the first stroke the user has made over a certain skin area. With a regular epilator this would mean that the user has again (and again) to epilate the same skin area to reach an acceptable result (e.g. 95% of all hairs present are epilated). In case the proposed attachment 1 is used. the user needs only to epilate the skin area a single time with a single stroke, as the blade 6 or the plurality of blades integrated in the blade block 5 shave off essentially all those hairs that remain in the skin in the first and only stroke the user has to perform. This leads to a substantial reduction of the time used for hair removal. Hairs that are only shaved grow back faster than plucked hairs, so that a user has (at least in the beginning) to more often use the epilator 100 with the proposed attachment 1, but hairs that are shaved the first time are most probably plucked the next time. In addition, using one or several shaving blades leads to an improved skin feeling. The use of a blade 6 leads to a smoother and cleaner skin feeling than with a pure plucking epilator. The smooth and clean skin feeling can even be improved by using a refreshing skin lotion, e.g. released from an applicator unit as discussed before.

The dimensions and values disclosed herein are not to be understood as being strictly limited to the exact numerical values recited. Instead, unless otherwise specified. each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention, It is therefore intended to cover in the appended claims all such changes and modifications that are within the scope of this invention.

What is claimed is:

1. An Epilator comprising
- a housing;
- an epilation cylinder mounted at a head region of the housing for plucking hairs from the skin during operation; and
- an attachment detachably connected with the housing, wherein the attachment comprises at least a shaving blade defining a use direction along which the shaving blade is to be drawn over the skin to shave off hairs, and in the attached state the shaving blade is disposed behind the epilation cylinder with respect to the use direction so that during operation the epilation cylinder plucks hairs from the skin and the shaving blade contacts the skin to shave off hairs from the skin in successive order during a single stroke of the epilator over a skin area, wherein the attachment is connected with the housing in the head region such that the epilation cylinder is partially covered by the attachment and a non-covered part of the epilation cylinder extends into an aperture of the attachment.

2. The Epilator according to claim 1, wherein the attachment comprises a first frame structure that has at least a connector structure for connecting the attachment with the head region of the housing and a second frame structure that comprises the shaving blade and the aperture and said second frame structure is mounted to the first frame structure such that it can swivel with respect to a swivel axis.

3. Epilator according to claim 2, wherein the second frame structure is detachably mounted to the first frame structure.

4. The Epilator according to claim 1, wherein the attachment comprises a first frame structure, a coupling structure, and a shaving blade cartridge, wherein the shaving blade cartridge comprises the shaving blade and is detachably coupled to the first frame structure via the coupling structure.

5. The Epilator according to claim 4, wherein the shaving blade cartridge is pivotably mounted with respect to the first frame structure.

* * * * *